US012446866B2

(12) United States Patent
Tam et al.

(10) Patent No.: US 12,446,866 B2
(45) Date of Patent: Oct. 21, 2025

(54) SAMPLING SYSTEM

(71) Applicant: Chi Chun Terence Tam, Hong Kong (CN)

(72) Inventors: Chi Chun Terence Tam, Hong Kong (CN); Mae Ann Michele Yuen, Hong Kong (CN)

(73) Assignee: Chi Chun Terence Tam, Hong Kong (CN)

( * ) Notice: Subject to any disclaimer, the term of this patent is extended or adjusted under 35 U.S.C. 154(b) by 982 days.

(21) Appl. No.: 17/618,860

(22) PCT Filed: Jun. 12, 2020

(86) PCT No.: PCT/CN2020/095843

§ 371 (c)(1),
(2) Date: Dec. 13, 2021

(87) PCT Pub. No.: WO2020/249090

PCT Pub. Date: Dec. 17, 2020

(65) Prior Publication Data

US 2022/0240908 A1 Aug. 4, 2022

(30) Foreign Application Priority Data

Jun. 14, 2019 (HK) ................................ 19125288.1

(51) Int. Cl.
*A61B 10/04* (2006.01)
*A61B 10/06* (2006.01)
*A61B 18/04* (2006.01)

(52) U.S. Cl.
CPC .............. *A61B 10/04* (2013.01); *A61B 10/06* (2013.01); *A61B 18/04* (2013.01)

(58) Field of Classification Search
None
See application file for complete search history.

(56) References Cited

U.S. PATENT DOCUMENTS 5,133,360 A 7/1992 Spears
5,217,458 A 6/1993 Parins
(Continued)

FOREIGN PATENT DOCUMENTS

CN 102258393 11/2011
CN 102379727 3/2012
(Continued)

OTHER PUBLICATIONS

Chinese Office Action of Serial No. 202080043359.0 dated Sep. 15, 2023, 7 pages.
(Continued)

*Primary Examiner* — Jay B Shah

(57) ABSTRACT

A sampling system (600) includes a sampling unit (50), a control unit (10), and a connecting tube (30). The sampling unit (50) is configured for acquiring a tissue sample. The control unit (10) is configured for controlling the working state of the sampling unit (50) and includes a first adjustment assembly (12). The first adjustment assembly (12) includes a first adjustment knob (120) and an actuating string (122), and the actuating string (122) is rigid. The connecting tube (30) is assembled with the control unit (10), with at least one end running through the control unit (10), and one end fixedly assembled with the sampling unit (50). Two ends of the actuating string (122) are respectively connected to the first adjustment knob (120) and the sampling unit (50). As such, the adjustment of the first adjustment knob (120) enables the actuating string (122) to move, to be pushed away or pulled back, thereby making the sampling unit (50) be opened or closed, to allow for the cutting and acquisition by the sampling unit (50) with safe and reliable operation.

9 Claims, 7 Drawing Sheets

600

(56) References Cited

U.S. PATENT DOCUMENTS

| | | | |
|---|---|---|---|
| 5,848,978 | A | 12/1998 | Cecchi |
| 2002/0169362 | A1 | 11/2002 | Kan et al. |
| 2005/0113854 | A1 | 5/2005 | Uckele |

FOREIGN PATENT DOCUMENTS

| | | | |
|---|---|---|---|
| JP | H05337114 | A | 12/1993 |
| JP | H1119086 | | 1/1999 |
| JP | 2018537135 | A | 12/2018 |
| WO | WO2019103694 | A1 | 5/2019 |

OTHER PUBLICATIONS

Extended European Search Report of S/N EP 20822627.4 dated May 23, 2023, 8 pages.

European Office Action of Serial No. 20 822 627.4 dated Feb. 15, 2024, 4 pages.

International Search Report and Written Opinion of PCT/CN2020/095843 dated Aug. 24, 2020, 12 pages (English and Chinese).

Japanese Office Action of JP2021-574767 dated Dec. 6, 2022, 3 pages.

SAMPLING SYSTEM

CROSS REFERENCE TO RELATED ART

The present application claims the priority to Hong Kong short-term Patent Application No. 19125288.1 filed with the Patent Registry, Intellectual Property Department, the Government of Hong Kong Special Administrative Region on Jun. 14, 2019 and entitled "Sampling System", which is incorporated herein by reference in its entirety.

TECHNICAL FIELD

Embodiments of the present disclosure relates to the technical field of medical devices, and particularly to a sampling system.

BACKGROUND

Endoscopy is an approach to obtain the type of lesion in a human body, which includes sampling a tissue in the human body by a sampling system to obtain a tissue sample and then examining the tissue sample to determine the type of lesion in a lesion site in the human body. During operation, a surgeon delivers the sampling system into a lesion site in a human body, acquires a sample from the tissue in the lesion site in the human body by an acquiring device on the sampling system to obtain a tissue sample, and examines the tissue sample, to acquire the cause and type of lesion in the lesion site in the human body.

At present, the sampling device on the sampling system is usually forceps or needle aspiration. However, the sample is often too shallow and/or small when the tissue sample is repeatedly taken by forceps or by needle aspiration; and if large-size and deep sampling (such as cryobiopsy) is adopted, significant bleeding is often caused, and the operation is not safe and reliable.

SUMMARY

The object of the embodiments of the present application is to provide a sampling system with safe and reliable operation.

To solve the above technical problem, the following technical solution is adopted in the present invention. A sampling system is provided, which includes:

a sampling unit, configured for acquiring a tissue sample;

a control unit, configured for controlling the working state of the sampling unit and including a first adjustment assembly, where the first adjustment assembly includes a first adjustment knob and an actuating string, and the actuating string is rigid; and a connecting tube, assembled to the control unit and having at least one end running through the control unit, and one end of the connecting tube being fixedly assembled to the sampling unit, wherein one end of the actuating string is fixed to the first adjustment knob and an other end of the actuating string is fixed to the sampling unit; and the sampling unit is controllable to be opened or closed by controlling the first adjustment knob.

Optionally, the sampling unit comprises a sampling sheath, a supporting portion and a heating member, wherein one end of the sampling sheath inserts into the connecting tube and connected to the connecting tube, and an other end of the sampling sheath is connected to the support portion; the support portion is deformable upon an external force, and the heating member is mounted around the sampling sheath; and the one end of the actuating string is fixed to the first adjustment knob and the other end of the actuating string is fixed to the heating member; the actuating string is controllable to move by controlling the first adjustment knob, whereby the heating member is controlled to be opened or closed, which in turn drives the support portion to be opened or closed.

Optionally, the connecting tube comprises a communicating tube, having at least one end extending through the control unit, wherein the one end of the sampling sheath inserts into the communicating tube and is connected to the communicating tube; and the communicating tube is provided with a receiving passage and an aperture, wherein the aperture is located in the control unit.

Optionally, the control unit comprises a conductive component having a cable sheath and a cable, wherein the cable sheath is fixedly mounted in the control unit, and the cable is partly located in the cable sheath and partly in the receiving passage, and the cable has one end electrically connected to the outside and an other end extending through the aperture and the receiving passage and electrically connected to the heating member.

Optionally, the connecting tube further comprises an endoscope tube and an outer sleeve, wherein at least one end of the endoscope tube extends through the control unit, and one end of the endoscope tube is assembled to the sampling sheath, the endoscope tube is movable relative to the control unit, and the outer sleeve is located outside the control unit and has one end assembled to the control unit; and the outer sleeve is mounted around the communicating tube, and the communicating tube is mounted around the endoscope tube.

Optionally, the sampling system further comprises a balloon unit having a balloon and a metal ring, wherein the balloon is mounted around the metal ring, and the metal ring is mounted around the connecting tube; and the balloon unit is located between the sampling unit and the control unit.

Optionally, the connecting tube further comprises a gas-liquid tube located between the outer sleeve and the communicating tube, and both the balloon and the metal ring are mounted around one end of the gas-liquid tube adjacent to the sampling unit.

Optionally, the control unit further comprises a linear rack and a second adjustment assembly, the linear rack is fixed to the communicating tube and the linear rack is parallel to the communicating tube; and the second adjustment assembly comprises a second adjustment knob and a third adjustment gear, the second adjustment knob is assembled to the third adjustment gear, and the third adjustment gear is drivable by the second adjustment knob to rotate; and wherein the second adjustment knob is assembled to the control unit, and the second adjustment knob is partially located in the control unit; and the third adjustment gear is located in the control unit and engaged with the linear rack.

Optionally, the control unit further comprises a conducting assembly having a balloon gas-liquid joint, wherein the balloon gas-liquid joint is communicated with the gas-liquid tube, and the balloon gas-liquid joint is provided with a balloon gas-liquid exchange port thereon;

the gas-liquid tube is provided with a first gas-liquid guide hole;

an inner wall of the balloon is connected to the gas-liquid tube and is provided with a first gas-liquid acquiring hole; and the first gas-liquid acquiring hole communicates with the first gas-liquid guide hole, and the balloon gas-liquid exchange port communicates with the first gas-liquid guide hole and an external environment.

Optionally, the conducting assembly further comprises a body gas-liquid joint, wherein the body gas-liquid joint is connected to the gas-liquid tube, and the body gas-liquid joint is provided with a body gas-liquid exchange port thereon;

the gas-liquid tube is provided with a second gas-liquid guide hole, and the second gas-liquid guide hole communicates with an internal environment; and the second gas-liquid guide hole communicates with the body gas-liquid exchange port, and the body gas-liquid exchange port communicates with the second gas-liquid guide hole and the external environment.

Embodiments of the present application have the following beneficial effects. The control unit and the sampling unit are connected through a connecting tube, the control unit is provided with a first adjustment assembly, and the first adjustment assembly includes a first adjustment knob and an actuating string. Two ends of the actuating string are respectively connected to the first adjustment knob and the sampling unit. Due to the rigidity and high hardness of the actuating string, by controlling the first adjustment knob, the movement of the actuating string is controlled to be pulled or loosened, so that the sampling unit can be opened and closed to enable the cutting and acquisition by sampling unit with safe and reliable operations.

BRIEF DESCRIPTION OF THE DRAWINGS

In FIGS. 1 to 10, 600 sampling system, 10 control unit, 20 endoscope connecting seat, 30 connecting tube, 40 balloon unit, 50 sampling unit, 11 housing, 12 first adjustment assembly, 13 linear rack, 14 second adjustment assembly, 15 balloon buffering assembly, 16 conductive component, 17 locking fin, 18 conducting assembly, 110 first opening, 111 second opening, 112 third opening, 113 clamping position, 114 blocking wall, 120 first adjustment knob, 121 connecting block, 140 second adjustment knob, 141 third adjustment gear, 150 magnetic damper, 151 mounting block, 152 spring, 160 cable sheath, 161 cable, 170 fixing portion, 171 clamping portion, 172 fixing hole, 180 body gas-liquid joint, 181 balloon gas-liquid joint, 182 gas-liquid tube connecting portion, 31 outer sheath, 32 gas-liquid tube, 33 communicating tube, 34 endoscope tube, 41 balloon, 42 metal ring, 51 sampling sheath, 52 support portion, 53 heating member, 54 support bar, 521 tongue, 531 first heating portion, 532 second heating portion, 55 outer ring, 56 inner ring, 57 heating piece, 58 metal strip, 59 insulating layer.

DESCRIPTION OF THE EMBODIMENTS

For facilitating the understanding of the present application, the present application will be described in further detail below with reference to the drawings and specific embodiments. It should be noted that when an element is described as being “fixed to” another element, it may be directly provided on the said element, or there can be one or more intervening elements therebetween. When an element is described as being “connected” to another element, it may be directly connected to the said element, or there may be one or more intervening elements therebetween. The terms “vertical”, “horizontal”, “left”, “right”, “inner”, “outer” and similar expressions used in this specification are for illustrative purposes only.

Unless defined otherwise, all technical and scientific terms used herein have the same meaning as commonly understood by a person skilled in the art to which the present application pertains. The terms used in the description of the present application are for the purpose of describing particular embodiments only and are not to limit the present application. The term “and/or” as used herein includes any and all combinations of one or more of the listed related items.

Figure 1:
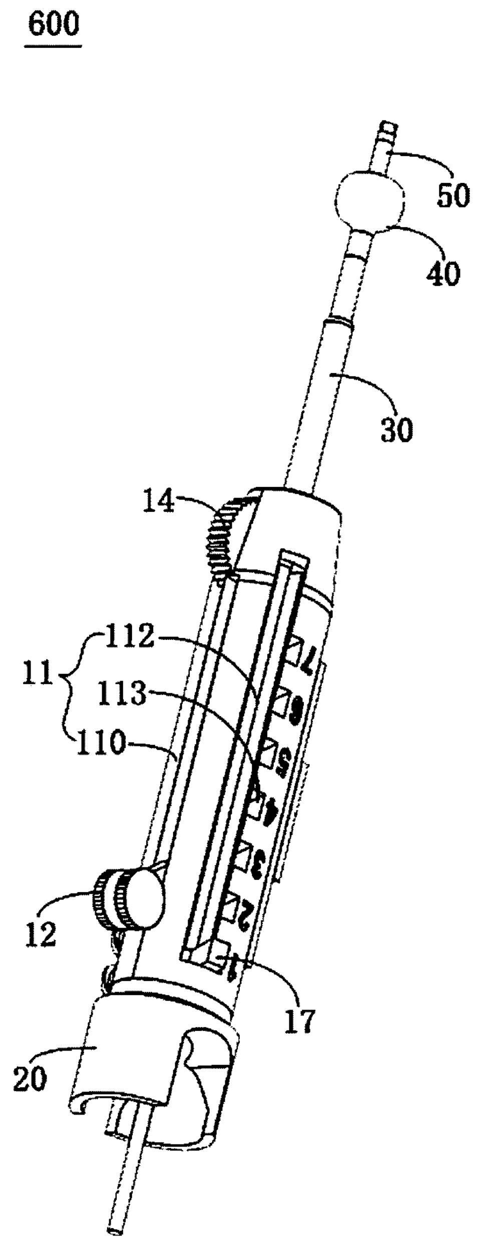
FIG. 1 is a schematic structural view of a sampling system in an embodiment of the present application.
Figure 2:
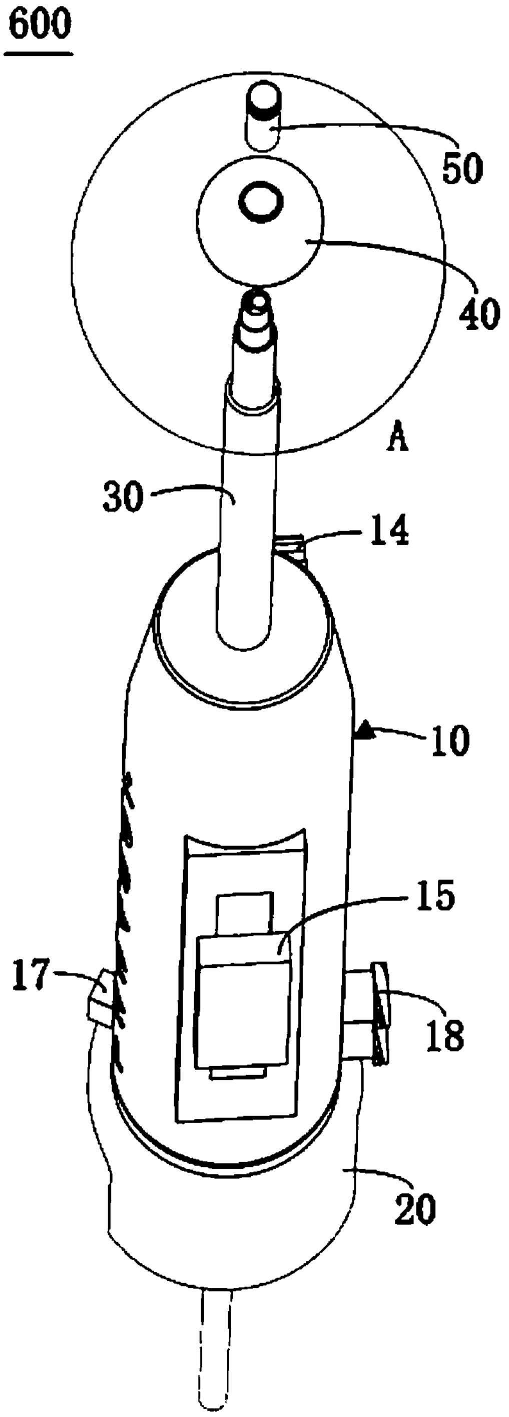
FIG. 2 is another schematic structural view of the sampling system shown in FIG. 1.

Referring to FIGS. 1 and 2, an embodiment of the present application provides a sampling system 600, which includes a control unit 10, an endoscope connecting seat 20, a connecting tube 30, a balloon unit 40 and a sampling unit 50. The control unit 10 is fixedly connected to the endoscope connecting seat 20. The connecting tube 30 has one end extending through the control unit 10 and is assembled thereto. The sampling unit 50 and the balloon unit 40 are both fixedly assembled to the connecting tube 30. The sampling unit 50 is located at one end of the connecting tube 30. The balloon unit 40 is located between the sampling unit 50 and the control unit 10. The sampling unit 50 and the balloon unit 40 is opposite to one end of the control unit 10, and the endoscope connecting seat 20 is located at the other end of control unit 10, In this embodiment, the control unit 10 is configured to adjust and control the working state and working position of the sampling unit 50 and the balloon unit 40.

Figure 3:
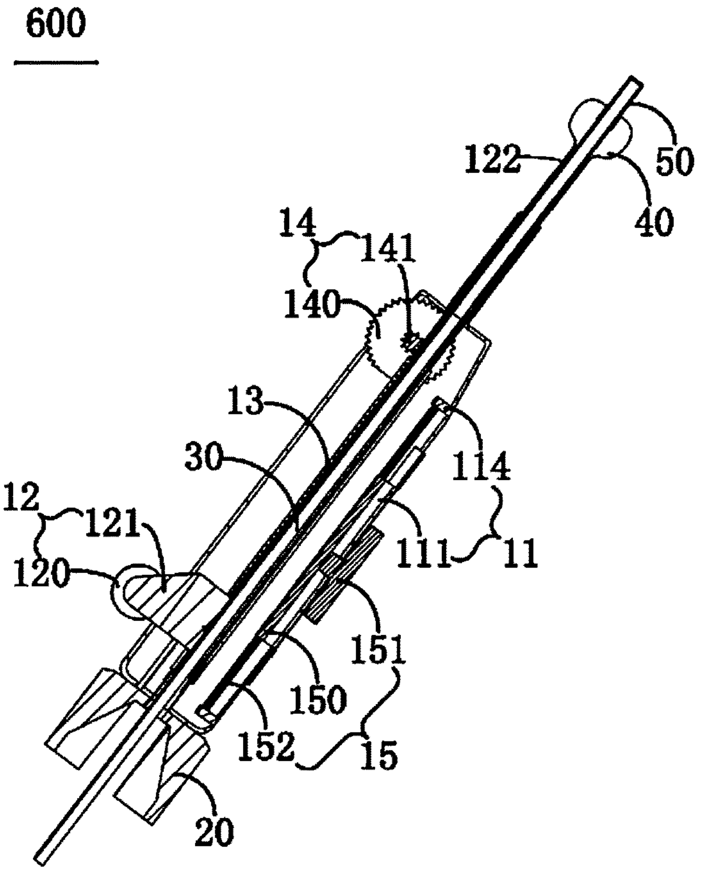
FIG. 3 is a cross-sectional view of the sampling system shown in FIG. 1.
Figure 4:
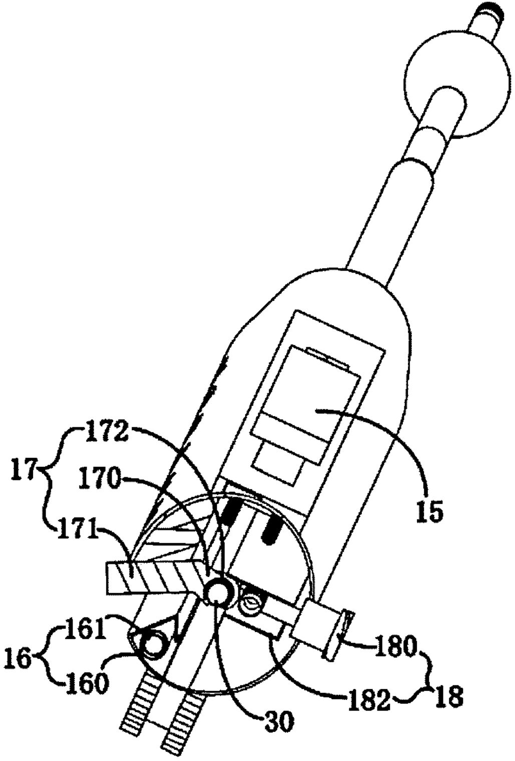
FIG. 4 is another cross-sectional view of the sampling system shown in FIG. 1.

Referring to FIGS. 3 and 4, the control unit 10 includes a housing 11, a first adjustment assembly 12, a linear rack 13, a second adjustment assembly 14, a balloon buffering assembly 15, a conductive component 16, a locking fin 17, and a conducting assembly 18. The linear rack 13 is located inside the housing 11. The first adjustment assembly 12, the second adjustment assembly 14, the conductive component 16, the locking fin 17, the conducting assembly 18 and the balloon buffering assembly 15 are all partially located inside the housing 11 and partly located outside the housing 11.

The housing 11 is configured for installing and accommodating other parts of the control unit 10. The housing 11 can be made of a plastic material, which has a light weight and prevents electric leakage.

The housing 11 is substantially cylindrical with a chamfer at one end. Both ends of the housing 11 are each provided with an opening. The housing has a hollow structure inside for partially accommodating other parts of the control unit 10 and partially accommodating the connecting tube 30. The housing 11 is provided with a first opening 110, a second opening 111, a third opening 112, at least one clamping position 113 and at least one blocking wall 114. The first opening 110, the second opening 111, the third opening 112 and the clamping position 113 all penetrate the housing 11. The first opening 110, the second opening 111, and the third opening 112 are all rectangular holes; and the first opening 110, the second opening 111 and the third opening 112 all extend along the length direction of the housing 11.

The at least one clamping position 113 is located at one side of the third opening 112, and includes a plurality of clamping positions 113. The plurality of clamping positions 113 are arranged side by side along the longitudinal direction of the third opening 112, and communicated with the third opening 112.

The at least one blocking wall 114 is located inside the housing 11. In this embodiment, two blocking walls 114 are provided, and the two blocking walls 114 are located at two ends of the housing 11 respectively.

One end of the housing 11 is assembled with the endoscope connecting seat 20. Optionally, the housing 11 and the endoscope connecting seat 20 can be assembled by welding, or by threaded connection via a threaded hole.

In this embodiment, the endoscope connecting seat 20 is configured fix mounting to other parts of the sampling system 600, so as to connect the housing 11 and other parts of the sampling system 600.

Further, the first adjustment assembly 12 is used to control the opening and closing of the sampling unit 50, and includes at least one first adjustment knob 120, at least one actuating string 122, and a connecting block 121, wherein two first adjustment knobs 120 are provided, and two actuating strings are provided correspondingly. The two first adjustment knobs 120 are both fitted to the connecting block 121, and are respectively located at two sides of the connecting block 121. The two first adjustment knobs 120 can rotate relative to the connecting block 121. The connecting block 121 is in contact with and connected to the connecting tube 30. The two actuating strings 122 are respectively fitted to the two first adjustment knobs 120. The controlling of the opening and closing of the sampling unit 50 can be achieved by rotating the two first adjustment knobs 120, For example, when the two first adjustment knobs 120 are rotated clockwise to wind the two actuating strings 122, the sampling unit 50 is opened. When the first adjustment knob 120 is rotated counterclockwise to loosen the two actuating strings 122, the sampling unit 50 is closed.

In this embodiment, the end of the actuating string 122 that is fitted to the sampling unit 50 is Y-shaped, and is fitted to the sampling unit 50 by welding or clamping.

The linear rack 13 is located inside the housing 11, and a portion of the connecting tube 30 is located inside the housing 11. The linear rack 13 is fixedly assembled with the portion of the connecting tube 30 located inside the housing 11. Further, the linear rack 13 is arranged along the length direction of and parallel to the connecting tube 30.

The second adjustment assembly 14 is configured to control the working positions of the sampling unit 50 and the balloon unit 40, and includes a second adjustment knob 140 and a third adjustment gear 141. The outer diameter of the second adjustment knob 140 is larger than that of the third adjustment gear 141, and the second adjustment knob 140 is assembled with the third adjustment gear 141. Optionally, the second adjustment knob 140 and the third adjustment gear 141 may be connected by a connecting rod. Alternatively, the second adjustment knob 140 and the third adjustment gear 141 may be assembled in other ways. The third adjustment gear 141 and the linear rack 13 are engaged with each other. When the second adjustment knob 140 is rotated, the third adjustment gear 141 is driven to rotate, thereby driving the linear rack 13 and the connecting tube 30 to move.

The balloon buffering assembly 15 is configured for assembly with an external structure during use, to fix the sampling system, or to stabilize the entire sampling system.

The balloon buffering assembly 15 includes a magnetic damper 150, a mounting block 151, and at least one spring 152. The magnetic damper 150 is assembled with the spring 152 and the mounting block 151, to compensate incidentally moving of the balloon unit 40 and the connecting tube 30, thus ensuring the balance of the entire sampling system 600.

Further, the magnetic damper 150 is in the form of a rectangular block structure, and the mounting block 151 is T-shaped. The magnetic damper 150 and the spring 152 are located inside the housing 11, and the mounting block 151 extends through the second opening 111 and is then fixedly assembled with the magnetic damper 150 located inside the housing 11. Optionally, the magnetic damper 150 and the mounting block 151 may be assembled by punching and screwing, or by other means.

In this embodiment, four springs 152 are provided, and the four springs 152 are all located in the housing 11 and are mounted in pairs on opposite two sides of the magnetic damper 150. Each spring 152 has one end abutting against the magnetic damper 150, and the other end abutting against the blocking wall 114.

In this embodiment, the housing 11 is further provided with a positioning member (not shown). The positioning member is located on the outer surface of the housing 11, and is fixed to the housing 11 and assembled with the balloon buffering assembly 15. The positioning member is also provided with an opening at a position aligned with the second opening 111. The mounting block 151 is partially extended through the opening in the positioning member and the second opening 111 and then fixedly assembled with the magnetic damper 150. The mounting block 151 is moveable relative to the positioning member.

Optionally, the positioning member has a reinforced connection and limiting function for the balloon buffering assembly 15. Of course, in other embodiments, the positioning member may be omitted.

Optionally, a plate-shaped wall of the housing 11 serves as a limiting wall (not shown), and the limiting wall together with another curved wall connected thereto defines a triangular receiving space. A cable 161 is partially received in the receiving space to prevent the cable 161 and other parts in the housing 11 from being in a mess.

Optionally, in some other embodiments, the conductive component 16 includes a cable sheath 160 and the cable 161. The limiting wall can be omitted. The cable sheath 160 has a hollow structure with two open ends, and is installed in the housing 11. The cable 161 is partially coiled in the cable sheath 160, and the cable sheath 160 is used to prevent the cable 161 located in the housing 11 from being in a mess. One end of the cable 161 is electrically connected to an external circuit system, and the other end is connected to the sampling unit 50. The sampling unit 50 is electrically connected to a circuit and electrically conducted by the cable 16. During the sampling process, the tissues and blood vessels will inevitably be harmed, and the coagulation of blood can be accelerated by the conduction and heating of the sampling unit 50, to control the bleeding, and ensure the safety of the sampling process.

One end of the cable 161 is electrically connected to an external circuit, and the other end extends through the connecting tube 30 to reach the sampling unit 50. Optionally, a hole for running the cable 161 is provided in the connecting tube 30. The cable 161 runs through the hole in the connecting tube 30 to reach and be electrically connected to the sampling unit 50.

The locking fin 17 is fixedly assembled with the connecting tube 30, and used to clamped with the clamping position 113 of the housing 11.

Specifically, the locking fin 17 includes a fixing portion 170 and an engaging portion 171, with an obtuse angle formed therebetween. This arrangement avoids the interference of the locking fin 17 with the movement of the connecting tube 30, and facilitates the clamping between the locking fin 17 and the clamping position 113.

The fixing portion 170 is provided with a fixing hole 172. The fixing hole 172 extends from one side of the fixing portion 170 toward the clamping portion 171, and has a semicircular shape. The fixing hole 172 is configured for fixedly assembly with the connecting tube 30. Specifically, the fixing portion 170 is mounted around and tightly fitted with the connecting tube 30 via the fixing hole 172. In this manner, the fixing portion 170 is fixed to the connecting tube 30, and accordingly the locking fin 17 is fixed to the connecting tube 30, so that when the locking fin 17 moves, it can drive the connecting tube 30 to move.

In this embodiment, the fixing portion 170 is mounted around the connecting tube 30 via the fixing hole 172, and the fixing portion 170 restricts the position of the locking fin 17 with respect to the connecting tube 30 by at least one elastic retainer ring. Two elastic retainer rings are provided, which are respectively located at upper and lower ends of the fixing portion 170 to fix the locking fin 17 and the connecting tube 30.

The clamping portion 171 is configured to fit with the clamping position 113 to limit the position of the connecting tube 30 with respect to the housing 11, that is, to limit the working positions of the sampling unit 50 and the balloon unit 40 with respect to the housing 11. When the connecting tube 30 moves to a certain position, the clamping portion 171 is clamped at the clamping position 113, to restrict and fix the connecting tube 30. As a result, the connecting tube 30 will not move due to an external force, thereby restricting and fixing the working position of the balloon unit 40.

Figure 5:
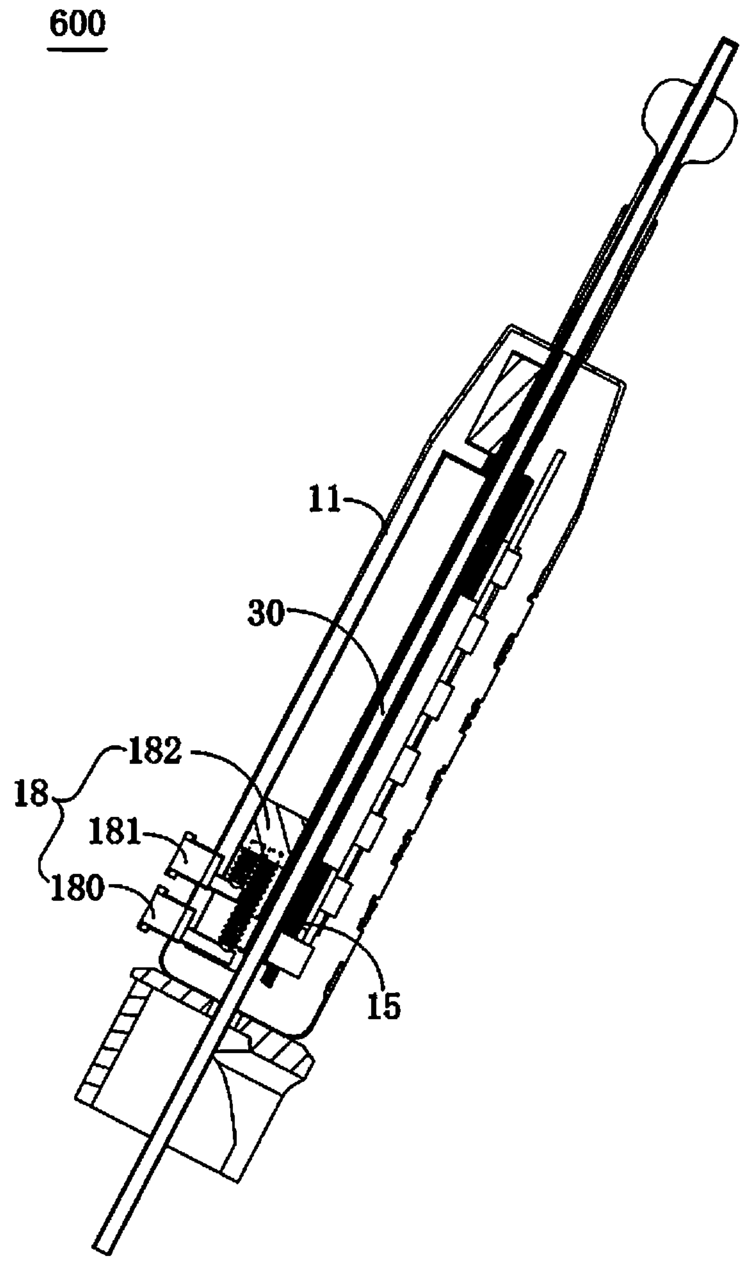
FIG. 5 is a further cross-sectional view of the sampling system shown in FIG. 1.

Referring to FIG. 5, the conducting assembly 18 includes a body gas-liquid joint 180, a balloon gas-liquid joint 181, and a gas-liquid tube connecting portion 182. The body gas-liquid joint 180 communicates with the internal environment of the human body and the gas and liquid in the body is exported to an external environment by the body gas-liquid joint 180. The balloon gas-liquid joint 181 communicates with the balloon unit, and the gas and liquid in the balloon unit 40 is exported to an external environment by the balloon gas-liquid joint 181. The gas-liquid tube connecting portion 182 is used to store part of the gas and liquid from the body and the balloon unit.

The gas-liquid tube connecting portion 182 is fixedly connected to the connecting tube 30, and communicated with the connecting tube 30. Optionally, the gas-liquid tube connecting portion 182 and the connecting tube 30 are provided with holes, via which they communicated with each other.

The human body and the balloon unit 40 are communicated by the connecting tube 30. The gas-liquid tube connecting portion 182 is provided with a storage cavity (not shown). The storage cavity is optionally divided into two separate parts that are respectively in communication with the gas-liquid joint 180 and the balloon gas-liquid joint 181. A part of the gas-liquid tube connecting portion 182 receives the gas and liquid introduced from the body, and the other part receives the gas and liquid introduced from the balloon unit 40. The gas-liquid tube connecting portion 182 is further provided with at least one first gas-liquid vent (not shown) and at least one second gas-liquid vent (not shown).

In this embodiment, two first gas-liquid vents and two second gas-liquid vents are provided. The two first gas-liquid vents and the two second gas-liquid vents are located separately at two separate parts of the gas-liquid tube connecting portion 182. The connecting tube 30 and the gas-liquid tube connecting portion 182 are communicated by one of the first gas-liquid vents, and the gas-liquid tube connecting portion 182 and the body gas-liquid joint 180 are communicated by the other of the first gas-liquid vent, to enable gas and liquid conduction. The connecting tube 30 and the gas-liquid tube connecting portion 182 are communicated by one of the second gas-liquid vents, and the gas-liquid tube connecting portion 182 and the balloon gas-liquid joint 181 are communicated by the other of the second gas-liquid vents, to achieve gas and liquid conduction.

The body gas-liquid joint 180 is provided with a body gas-liquid exchange port (not shown) correspondingly, and the body gas-liquid exchange port communicates with the two first gas-liquid vents. By the body gas-liquid exchange port, the gas and liquid in the body are allowed to flow to the external environment, or the gas and liquid in the external environment is allowed to be introduced into the body.

The balloon gas-liquid joint 181 is provided with a balloon gas-liquid exchange port (not shown) correspondingly, and the balloon gas-liquid exchange port communicates with the two second gas-liquid vents. By the balloon gas-liquid exchange port, the gas and liquid in the balloon unit 40 are allowed to be introduced to the external environment, or the gas and liquid in the external environment is allowed to be introduced into the balloon.

Optionally, the balloon gas-liquid exchange port may be connected, by a tube, to an external device, for example, an oxygen supply device or a ventilation device.

Optionally, in this embodiment, a thin tube (not shown) is provided in the gas-liquid tube connecting portion 182 and the connecting tube 30. The thin tube has a hollow tubular structure with two open ends. The connecting tube 30 and the gas-liquid tube connecting portion 182 are provided with a hole for the thin tube extending through. The thin tube is partly located in the connecting tube 30, and partly located in the gas-liquid tube connecting portion 182. The thin tube allows the liquid and gas to flow between the connecting tube 30 and the gas-liquid tube connecting portion 182.

Figure 6:
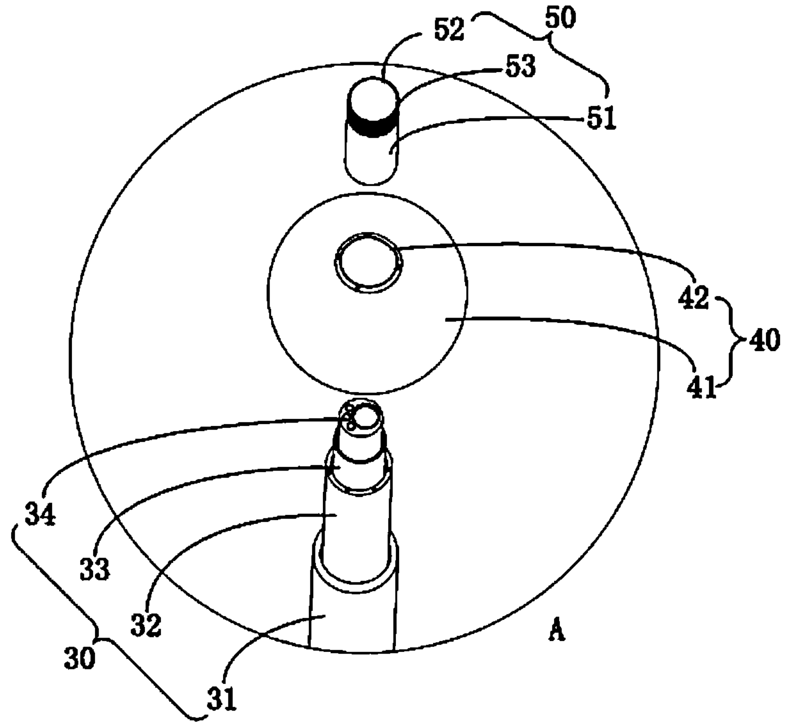
FIG. 6 is a partially enlarged view of the sampling system shown in FIG. 2.

Referring to FIG. 6, the connecting tube 30 is made of a transparent material and includes an outer sheath 31, a gas-liquid tube 32, a communicating tube 33 and an endoscope tube 34. The outer sheath 31 is located at the outermost side, and the endoscope tube 34 is located at the innermost side. The gas-liquid tube 32 and the communicating tube 33 are located between the outer sheath 31 and the endoscope tube 34. Moreover, the gas-liquid tube 32 is closer to the outer sheath 31 than the communicating tube 33, and the communicating tube 33 is closer to the endoscope tube 34 than the gas-liquid tube 32. The length of the outer sheath 31 is shorter than those of the gas-liquid tube 32 and the communicating tube 33.

The outer sheath 31 protects other tubes inside, and one end of the outer sheath 31 is fixed to one end of the housing 11.

The gas-liquid tube 32 is used to conduct the liquid and gas. In this embodiment, the gas-liquid tube 32 communicates with the gas-liquid tube connecting portion 182 of the conducting assembly 18. Specifically, the gas-liquid tube 32 is provided with a first gas-liquid guide hole (not shown) and a second gas-liquid guide hole (not shown). The center line of the first gas-liquid guide hole is parallel to the center line of the second gas-liquid guide hole.

In this embodiment, the first gas-liquid guide hole communicates with the two first gas-liquid vents, and the first gas-liquid guide hole communicates with the balloon gas-liquid exchange port. The second gas-liquid guide hole communicates with the two second gas-liquid vents, and the second gas-liquid guide hole communicates with the body gas-liquid exchange port.

The communicating tube 33 is used to lead the actuating string 122 and the cable 161 to the sampling unit 50, so that the actuating string 122 can be assembled with the sampling unit 50, and the cable 161 and the sampling unit 50 can be electrically connected.

In this embodiment, the linear rack 13 is fixedly assembled with the communicating tube 33, and engaged with the third adjustment gear 141 of the second adjustment assembly 14. By rotating the second adjustment knob 140, the third adjustment gear 141 and the linear rack 13 interact with each other to drive the communicating tube 33 to move.

Optionally, in this embodiment, a plurality of receiving passages (not shown) and a plurality of apertures (not shown) are provided in the communicating tube 33. The plurality of receiving passages are used to receive the actuating string 122 and the cable 161, and the plurality of apertures are configured for the actuating string 122 and the cable 161 extending through, to realize the connection of the actuating string 122 and the cable 161 to the sampling unit 50.

The endoscope tube 34 is actually a part of an endoscope, and has one end equipped with a camera device for taking pictures of the environment in the body, so that the physician can judge the sampling state and the condition in the body.

In this embodiment, the endoscope tube 34 can move relative to the control unit 10. Specifically, the endoscope tube 34 can move relative to the housing 11 to take pictures of the environment in the body.

The balloon unit 40 includes a balloon 41 and a metal ring 42. The balloon 41 is made of a plastic material with an elastic deformation characteristic, and used to accommodate a gas and liquid. The metal ring 42 is used to prompt or indicate the position of the balloon 41, Optionally, the balloon 41 and the metal ring 42 are both mounted around the gas-liquid tube 32 at one end close to the sampling unit 50, without communicating with the balloon gas-liquid joint 181 and the body gas-liquid joint 180.

Specifically, in this embodiment, the metal ring 42 is mounted around the gas liquid tube 32, and the gas-liquid tube 32 is provided with a first gas-liquid acquiring hole (not shown) at a position corresponding to the first gas-liquid guide hole.

In this embodiment, the gas and liquid in the balloon 41 flow in from the first gas-liquid acquiring hole of the gas-liquid tube 32, and flow to the balloon gas-liquid exchange port via the first gas-liquid guide hole and the two first gas liquid vents in sequence and finally to the external environment or to the other device connected to the balloon gas-liquid joint 181. Alternatively, the gas and liquid can flow into the balloon unit 40 from a reverse direction.

When sampling, the gas and liquid in the body flow in from the second gas-liquid guide hole, and flow to body gas-liquid exchange port via the two second gas-liquid vents and finally to the external environment. Alternatively, the gas and liquid can flow into the body from a reverse direction.

In this embodiment, the fixing portion 170 is mounted around the gas-liquid tube 32 through the fixing hole 172, and closely fits with the gas-liquid tube 32, to fix the fixing portion 170 and the gas-liquid tube 32. That is, the locking fin 17 and the gas-liquid tube 32 are fixed, so that the gas-liquid tube 32 can temporarily lock the positions of the balloon 41 and the gas-liquid tube 32 before the balloon 41 expands. After the balloon 41 expands, the locking of the position of the locking fin 17 can be released.

Figure 7:
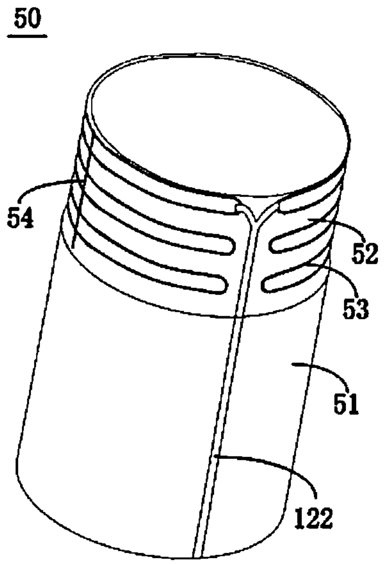
FIG. 7 is a reference view showing the state of a sampling unit in the sampling system shown in FIG. 6.
Figure 8:
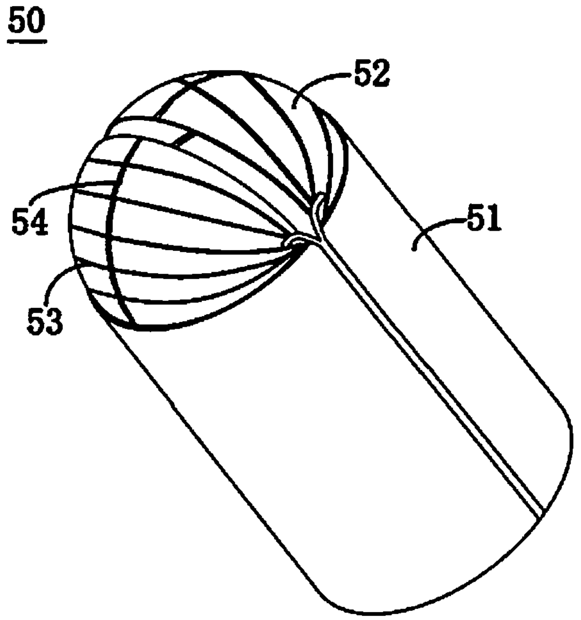
FIG. 8 is another reference view showing the state of the sampling unit in the sampling system shown in FIG. 6.

Referring to FIGS. 7 and 8, the sampling unit 50 includes a sampling sheath 51, a support portion 52, a heating member 53 and at least one support bar 54.

The sampling sheath 51 is mounted around the endoscope tube 34 and assembled with the endoscope tube 34. Moreover, the sampling sheath 51 is made of a relatively hard material, and used to install the support portion 52, to support and protect the support portion 52.

In this embodiment, the support portion 52 is a plastic molded member that is deformable by an external force, and is made of a plastic material with a certain hardness. The support portion 52 includes two parts, which are located on two sides of the same end of the sampling sheath 51. Two support bars 54 are provided, and the two support bars 54 are respectively assembled with the two parts of the support portion 52, to support the support portion 52, so that the support portion 52 can maintain its shape after being expanded.

Optionally, there may be more than two support bars 54.

The heating member 53 is mounted around the support portion 52. Optionally, a part of the heating member 53 is inserted and fixed in the sampling sheath 51, and the other part is mounted around the support portion 52.

It should be noted that in this embodiment, the heating member 53 also includes two parts. The two parts of the heating member 53 are respectively mounted around the outer surfaces of the two parts of the support portion 52. The two parts of the heating member 53 are fixedly assembled with the actuating strings 122, and the entire heating member 53 is opened and closed by controlling the movement of the actuating strings 122.

The heating member 53 is a heating coil, and the heating coil includes two parts. The two parts of the heating coil are respectively mounted around the two parts of the support portion 52. The two parts of the heating coil are deformable upon an external force. Normally, the two parts of the heating coil are wound into a cylindrical shape. One end of the actuating string 122 is assembled with the ends of the two parts of the heating coil that is away from the sampling sheath 51. Optionally, one end of the actuating string 122 is assembled with the ends of the heating coil away from the sampling sheath 51 by hooking.

When the first adjustment knob 120 is rotated clockwise, the actuating string 122 is pulled. The two parts of the heating coil are pulled, such that the entire heating member 53 is in a hemispheric shape (as shown in FIG. 8), the heating member 53 is closed, and the heating member 53 drives the support portion 52 to close at the same time. When the first adjustment knob 120 is rotated counterclockwise, the actuating string 122 is loosened, and without a pulling force, the two parts of the heating coil is unstressed, and returns to a cylindrical shape (as shown in FIG. 7). As a result, the heating member 53 opens, and the heating member 53 drives the support portion 52 to open.

When the heating member 53 is opened and closed, it drives the support portion 52 to open and close. The heating member 53 is connected to the cable 161 to realize electrical connection with an external circuit and realize heat generation. In this manner, the bleeding can be controlled, ensuring the safety of the sampling process.

Figure 9:
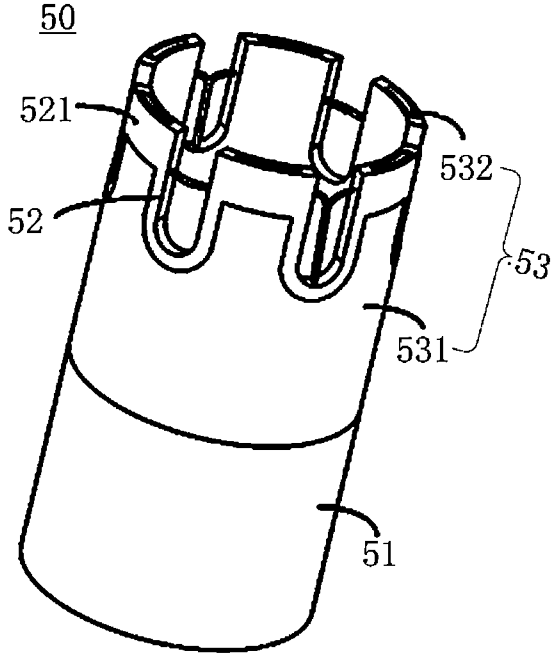
FIG. 9 is another reference view showing the state of the sampling unit in the sampling system shown in FIG. 7.

It should be noted that in this embodiment, it is the heating member 53, instead of the support portion 52, that is used to cut the tissue. The support portion 52 is used to support the heating member 53, to prevent the heating member 53 from being in a mess, and serves to collect the tissues cut by the heating member 53. Referring to FIG. 9, in some other embodiments, the support portion 52 is a plastic molded member. One end of the support portion 52 is fixedly assembled with the sampling sheath 51. The support portion 52 is electrically insulating and has a cylindrical shape. The end of the support portion 52 away from the sampling sheath 51 is cut to form a plurality of tongues 521, and the tongues 521 are electrically insulating. The heating member 53 includes a first heating portion 531 and a second heating portion 532. The first heating portion 531 is similar in shape to the support portion 52, and is mounted around the outer surface of the support portion 52. The second heating portion 532 is embedded in the tongue 521. The actuating string 122 is in the form of a lasso. The actuating string 122 is partially embedded in the support portion 52, and the portion of the actuating string 122 embedded in the support portion 52 is annular. A portion of the actuating string 122 runs along the connecting tube 30 through the support portion 52, and extends to the first adjustment assembly 12 for assembly with the first adjustment knob 120.

Optionally, the support bar 54 may not be rigid.

When the first adjustment knob 120 is rotated clockwise, the actuating string 122 is pulled, and the tongues 521 on the support portion 52 are pulled at the same time. The tongues 521 are bent in the same direction, so that the entire support portion 52 is in a closed state. When the first adjustment knob 120 is rotated counterclockwise, the actuating string 122 is unstressed, so that the tongues 521 are subjected to no force, and thus returns to its initial shape, and slowly becomes straight, making the entire support portion 52 in an open state.

Optionally, a non-thermal conductive layer (not shown) is provided between the first heating portion 531 and the sampling sheath 51 to separate the sampling sheath 51 and the first heating portion 531 to protect the sampling sheath 51 against influence by the first heating portion 531.

Figure 10:
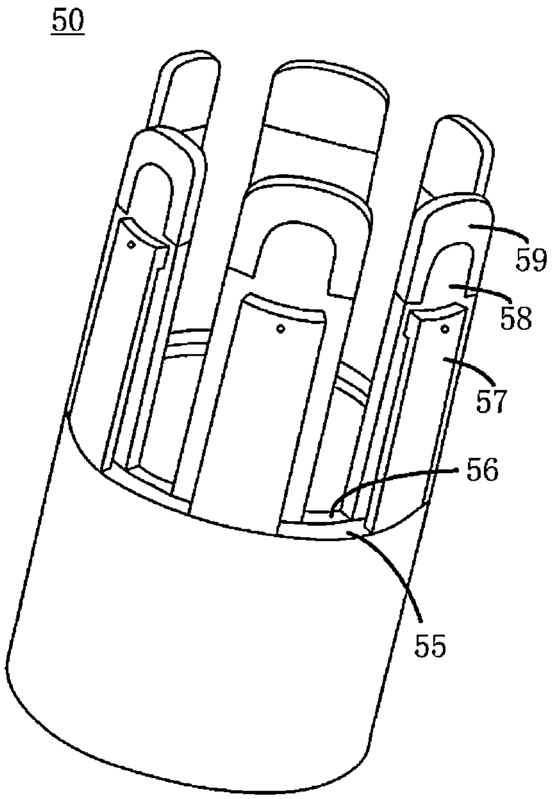
FIG. 10 is a further reference view showing the state of the sampling unit in the sampling system shown in FIG. 7.

Referring to FIG. 10, in another embodiment, the sampling unit 50 does not include the sampling sheath 51, the support portion 52, the heating member 53 and the support bar 54. Instead, the sampling unit 50 includes an outer ring 55, an inner ring 56, at least one heating piece 57, at least one metal strip 58, and an insulating layer 59.

The outer ring 55 and the inner ring 56 are both connected to the communicating tube 33, and the outer ring 55 and the inner ring 56 are both rotatable relative to the communicating tube 33.

Optionally, the communicating tube 33, the outer ring 55 and the inner ring 56 are provided with a receiving passage (not shown) for receiving the actuating string 122. The outer ring 55 and the inner ring 56 each have a hollow cylindrical shape with two open ends. The outer ring 55 and the inner ring 56 each are further provided with an annular tube (not shown) respectively at the end away from the communicating tube 33. The receiving passages are perpendicular to the annular tubes. One end of the actuating string runs through the communicating tube 33, and the receiving passages of the outer ring 55 and the inner ring 56, and is then fixed in the annular tubes. Optionally, the annular tubes of the outer ring 55 and the inner ring 56 each are provided with an opening (not shown).

In this embodiment, two actuating strings 122 are provided, which are respectively an outer ring actuating string and an inner ring actuating string. The sampling system 600 is provided with a gear (not shown) for controlling the actuating string. Two gears are provided, which are both installed on the control unit 10, and are respectively an outer ring gear and an inner ring gear.

The outer ring gear is used to control the state of the outer ring actuating string. The outer ring actuating string surrounds the outer ring gear, and two ends of the outer ring actuating string respectively pass through the receiving passage and enter the annular tube from the opening of the annular tube of the outer ring. The two ends enter the annular tube in two opposite directions, and are both fixed in the annular tube so that the portion of the outer ring actuating string located in the annular tube is ring-shaped.

By rotating the outer ring gear, the positions of two portions of the actuating string respectively on two sides of the outer ring gear is controlled, to control the positions of the two ends of the outer ring actuating string, so as to rotate the outer ring 55.

Similarly, the inner ring gear is used to control the state of the inner ring actuating string. The inner ring actuating string surrounds the inner ring gear, and two ends of the inner ring actuating string respectively pass through the receiving passage and enter the annular tube from the opening of the annular tube of the inner ring. The two ends enter the annular tube in two opposite directions, and are both fixed in the annular tube so that the portion of the inner ring actuating string located in the annular tube is ring-shaped.

By rotating the inner ring gear, the positions of two portions of the actuating string respectively on two sides of the inner ring gear is controlled, to control the positions of the two ends of the inner ring actuating string, so as to rotate the outer ring 56.

Further, by rotating the outer ring gear, the inner ring gear can be driven to rotate in an opposite direction. Therefore, in this embodiment, the inner ring gear and the outer ring gear rotate in opposite directions.

Further, one end of the heating piece 57 is fixed to one end of the outer ring 55, and one end of the metal strip 58 is fixed to one end of the inner ring 56. Optionally, six heating pieces 57 and six metal strips 58 are provided, and the six heating pieces 57 and six metal strips 58 are annularly arranged. Of course, other number of heating pieces 57 and metal strips 58 can be provided, which are not limited herein.

The sampling unit 50 also includes a fastener (not shown). Optionally, six fasteners are provided. Each heating piece 57 and one corresponding metal strip 58 are fixedly connected by one fastener. In addition, the heating piece 57 and the metal strip 58 are rotatable, and the fastener is located on an end of the heating piece 57 away from the outer ring 55.

The insulating layer 59 is mounted on the metal strip 58 to provide insulation and protection. Optionally, an air insulating layer is provided between the heating piece 57 and the metal strip 58.

The outer ring gear and the inner ring gear are rotated, and the outer ring 55 and the inner ring 56 are driven to move by controlling the rotation positions of the two ends of the outer ring actuating string and the inner ring actuating string. When the outer ring 55 and the inner ring 56 rotate in opposite directions, the heating piece 57 and the metal strip 58 are driven to rotate in opposite directions. The heating piece 57 and the metal strip 58 are fixed by the fastener, so that the heating piece 57 and the metal strip 58 are bent. The heating piece 57 and the metal strip 58 are both bent in the same direction, so that the sampling unit 50 is closed, and sampling is implemented. Correspondingly, when the outer ring gear and the inner ring gear are rotated, the outer ring 55 and the inner ring 56 rotate in the reverse directions, the heating piece 57 and the metal strip 58 rotate in the other directions, and then the heating piece 57 and the metal strip 58 slowly return to their original shape, so that the sampling unit 50 is opened. In this embodiment, an assembling procedure is to assemble the balloon unit 40 and the connecting tube 30, then assemble the sampling unit 50 and the connecting tube 30, next assemble the connecting tube 30 and the control unit 10, and finally assemble the endoscope connecting seat 20 and the control unit 10.

In the technical solution of the present application, the sampling system 600 includes the control unit 10, the connecting tube 30, and the sampling unit 50. The control unit 10 and the sampling unit 50 are both assembled with the connecting tube 30; and the control unit 10 is provided with the first adjustment assembly 12, and the first adjustment assembly 12 is provided with the first adjustment knob 120, the connecting block 121, and the actuating string. The actuating string is rigid, the first adjustment knob 120 and the connecting block 121 are assembled, and the first adjustment knob 120 is rotatable. The sampling unit 50 has the sampling sheath 51, the support portion 52, and the heating member 53. The sampling sheath 51 and the connecting tube 30 are fixedly assembled, the support portion 52 and the sampling sheath 51 are assembled, and the heating member 53 is mounted around the support portion 52. One end of the actuating string is assembled with the first adjustment knob 120, and the other end is fixed with the heating member 53. By rotating the first adjustment knob 120, the actuating string is wound or loosened, to control the heating member 53 to be opened or closed, thereby realizing the cutting and acquisition of internal tissues, with convenient, safe and reliable operations.

Further, the control unit 10 further includes the conductive component 16, and the conductive component 16 includes the cable 161. The cable 161 is connected to the heating member 53 through the connecting tube 30, so the heating member 53 can be energized to generate heat, thereby controlling the bleeding and ensuring the safety of the sampling process.

Further, the sampling system 600 further includes the balloon unit 40, and the control unit 10 is also provided with the second adjustment assembly 14 and the linear rack 13. The second adjustment assembly 14 is engaged with the linear rack 13. By adjusting the second adjustment assembly 14, the position of the sampling unit 50 relative to the control unit 10 can be controlled, to remain the positions of the gas-liquid tube 32 and the balloon unit 40.

It should be noted that preferred embodiments of the present application are given in the specification and drawings of the present application. However, the present application can be implemented in many different forms and, is not limited to the embodiments described in the specification. These embodiments cause no additional restrictions on the disclosure of the present application, are provided for thorough and comprehensive understanding of the disclosure of the present application, in addition, the above technical features can be combined with each other to form various embodiments not listed above, which are all contemplated in the scope of the description of the present disclosure. Further, modifications and changes can be made by those skilled in the art in accordance with the above description, which are intended to be contemplated in the protection scope of the appended claims.

What is claimed is:

1. A sampling system, comprising:

a sampling unit, configured for acquiring a tissue sample;

a control unit, configured for controlling a working state of the sampling unit and comprising a first adjustment assembly, wherein the first adjustment assembly comprises a first adjustment knob and an actuating string, and the actuating string is rigid; and a connecting tube, assembled to the control unit and having at least one end running through the control unit, and one end of the connecting tube being fixedly assembled to the sampling unit, wherein one end of the actuating string is fixed to the first adjustment knob and an other end of the actuating string is fixed to the sampling unit; and the sampling unit is controllable to be opened or closed by controlling the first adjustment knob;

the sampling unit comprises a sampling sheath, a supporting portion and a heating member, wherein one end of the sampling sheath inserts into the connecting tube and connected to the connecting tube, and an other end of the sampling sheath is connected to the support portion; the support portion is deformable upon an external force, and the heating member is mounted around the sampling sheath; and the one end of the actuating string is fixed to the first adjustment knob and the other end of the actuating string is fixed to the heating member; the actuating string is controllable to move by controlling the first adjustment knob, whereby the heating member is controlled to be opened or closed, which in turn drives the support portion to be opened or closed.

2. The sampling system according to claim 1, wherein the connecting tube comprises a communicating tube, having at least one end extending through the control unit, wherein the one end of the sampling sheath inserts into the communicating tube and is connected to the communicating tube; and the communicating tube is provided with a receiving passage and an aperture, wherein the aperture is located in the control unit.

3. The sampling system according to claim 2, wherein the control unit comprises a conductive component having a cable sheath and a cable, wherein the cable sheath is fixedly mounted in the control unit, and the cable is partly located in the cable sheath and partly in the receiving passage, and the cable has one end electrically connected to the outside and an other end extending through the aperture and the receiving passage and electrically connected to the heating member.

4. The sampling system according to claim 2, wherein the connecting tube further comprises an endoscope tube and an outer sleeve, wherein at least one end of the endoscope tube extends through the control unit, and one end of the endoscope tube is assembled to the sampling sheath, the endoscope tube is movable relative to the control unit, and the outer sleeve is located outside the control unit and has one end assembled to the control unit; and the outer sleeve is mounted around the communicating tube, and the communicating tube is mounted around the endoscope tube.

5. The sampling system according to claim 4, wherein the sampling system further comprises a balloon unit having a balloon and a metal ring, wherein the balloon is mounted around the metal ring, and the metal ring is mounted around the connecting tube; and the balloon unit is located between the sampling unit and the control unit.

6. The sampling system according to claim 5, wherein the connecting tube further comprises a gas-liquid tube located between the outer sleeve and the communicating tube, and both the balloon and the metal ring are mounted around one end of the gas-liquid tube adjacent to the sampling unit.

7. The sampling system according to claim 6, wherein the control unit further comprises a linear rack and a second adjustment assembly, the linear rack is fixed to the communicating tube and the linear rack is parallel to the communicating tube; and the second adjustment assembly comprises a second adjustment knob and a third adjustment gear, the second adjustment knob is assembled to the third adjustment gear, and the third adjustment gear is drivable by the second adjustment knob to rotate; and wherein the second adjustment knob is assembled to the control unit, and the second adjustment knob is partially located in the control unit; and the third adjustment gear is located in the control unit and engaged with the linear rack.

8. The sampling system according to claim 6, wherein the control unit further comprises a conducting assembly having a balloon gas-liquid joint, wherein the balloon gas-liquid joint is communicated with the gas-liquid tube, and the balloon gas-liquid joint is provided with a balloon gas-liquid exchange port thereon;

the gas-liquid tube is provided with a first gas-liquid guide hole;

an inner wall of the balloon is connected to the gas-liquid tube and is provided with a first gas-liquid acquiring hole; and the first gas-liquid acquiring hole communicates with the first gas-liquid guide hole, and the balloon gas-liquid exchange port communicates with the first gas-liquid guide hole and an external environment.

9. The sampling system according to claim 8, wherein the conducting assembly further comprises a body gas-liquid joint, wherein the body gas-liquid joint is connected to the gas-liquid tube, and the body gas-liquid joint is provided with a body gas-liquid exchange port thereon;

the gas-liquid tube is provided with a second gas-liquid guide hole, and the second gas-liquid guide hole communicates with an internal environment; and the second gas-liquid guide hole communicates with the body gas-liquid exchange port, and the body gas-liquid exchange port communicates with the second gas-liquid guide hole and the external environment.

* * * * *